(12) United States Patent  (10) Patent No.: US 8,416,405 B2
Panza et al.  (45) Date of Patent: Apr. 9, 2013

(54) RAMAN CHEMICAL IMAGING OF IMPLANTABLE DRUG DELIVERY DEVICES

(75) Inventors: Janice Panza, Pittsburgh, PA (US); John Maier, Pittsburgh, PA (US)

(73) Assignee: ChemImage Corporation, Pittsburgh, PA (US)

(*) Notice: Subject to any disclaimer, the term of this patent is extended or adjusted under 35 U.S.C. 154(b) by 237 days.

(21) Appl. No.: 12/537,671

(22) Filed: Aug. 7, 2009

(65) Prior Publication Data

US 2010/0033717 A1  Feb. 11, 2010

Related U.S. Application Data

(60) Provisional application No. 61/188,351, filed on Aug. 8, 2008, provisional application No. 61/026,951, filed on Feb. 6, 2009.

(51) Int. Cl.
*G01J 3/44* (2006.01)

(52) U.S. Cl. ............ 356/301; 356/328; 356/334; 435/4; 435/5; 435/32; 600/478

(58) Field of Classification Search .................. 356/301, 356/328–334; 435/4, 5, 32, 25, 39; 600/607, 600/600, 473–478
See application file for complete search history.

(56) References Cited

U.S. PATENT DOCUMENTS

| | | | |
|---|---|---|---|
| 4,080,073 A | 3/1978 | Wolga | |
| 4,564,761 A | 1/1986 | Buckwald | |
| 4,696,896 A | 9/1987 | Brinton | |
| 5,004,681 A | 4/1991 | Boyse | |
| 5,239,169 A | 8/1993 | Thomas | |
| 5,539,517 A | 7/1996 | Cabib | |
| 5,580,714 A | 12/1996 | Polovina | |
| 5,687,730 A | 11/1997 | Doiron | |
| 5,784,162 A | 7/1998 | Cabib | |

(Continued)

FOREIGN PATENT DOCUMENTS

| EP | 1990639 | 11/2008 |
|---|---|---|
| JP | 09121889 | 5/1997 |

(Continued)

OTHER PUBLICATIONS

Van De Poll, S.W.E. et al, "Artheriosclerosis, Thrombosis, and Vascular Biology," 2001, 21, 1630-1635 and supplementary information.

(Continued)

*Primary Examiner* — Gregory J Toatley
*Assistant Examiner* — Iyabo S Alli

(57) ABSTRACT

A system and method of determining an attribute of a biological tissue sample or a drug delivery device. A sample is illuminated with substantially monochromatic light to thereby generate Raman scattered photons. The Raman scattered photons are assessed to thereby generate a spectroscopic data set wherein said spectroscopic data set comprises at least one of: a Raman spectra and a spatially accurate wavelength resolved image. The spectroscopic data set is evaluated to determine at least one of: an attribute of a biological tissue sample and a drug delivery device. In one embodiment, the biological tissue comprises arterial tissue. In another embodiment, the drug delivery device is a drug-eluting stent. In another embodiment, Raman chemical imaging can be used to evaluate a sample and identify at least one of: the tissue, a drug, a drug delivery device, and a matrix associated with a drug delivery device.

18 Claims, 14 Drawing Sheets

U.S. PATENT DOCUMENTS

| | | | |
|---|---|---|---|
| 5,866,430 | A | 2/1999 | Grow |
| 5,919,135 | A | 7/1999 | Lemelson |
| 5,991,653 | A | 11/1999 | Richards-Kortum |
| 6,002,476 | A | 12/1999 | Treado |
| 6,040,906 | A | 3/2000 | Harhay |
| 6,070,583 | A | 6/2000 | Perelman |
| 6,091,985 | A | 7/2000 | Alfano |
| 6,174,291 | B1 | 1/2001 | McMahon |
| 6,201,989 | B1 | 3/2001 | Whitehead |
| 6,205,354 | B1 | 3/2001 | Gellerman |
| 6,283,236 | B1 | 9/2001 | Koenign |
| 6,424,859 | B2 | 7/2002 | Jaskcon |
| 6,449,087 | B2 | 9/2002 | Ogino |
| 6,485,413 | B1 | 11/2002 | Bopparty |
| 6,586,246 | B1 | 7/2003 | Yoon |
| 6,681,133 | B2 | 1/2004 | Chaiken |
| 6,697,665 | B1 | 2/2004 | Rava |
| 6,788,965 | B2 | 9/2004 | Ruchti |
| 6,826,422 | B1 | 11/2004 | Modell |
| 6,827,926 | B2 | 12/2004 | Robinson et al. |
| 6,949,081 | B1 * | 9/2005 | Chance .................. 382/181 |
| 6,950,184 | B2 | 9/2005 | Stewart |
| 7,478,008 | B2 | 1/2009 | Balss et al. |
| 7,515,952 | B2 | 4/2009 | Balas |
| 7,521,254 | B2 | 4/2009 | Pryce-Lewis et al. |
| 7,564,541 | B2 * | 7/2009 | Tuschel .................. 356/301 |
| 7,668,587 | B2 | 2/2010 | Benaron |
| 7,697,576 | B2 | 4/2010 | Maier |
| 2001/0044129 | A1 | 11/2001 | Ling |
| 2003/0018272 | A1 | 1/2003 | Treado |
| 2003/0105069 | A1 | 6/2003 | Robinson et al. |
| 2003/0133105 | A1 | 7/2003 | Gorelik et al. |
| 2003/0143580 | A1 | 7/2003 | Straus |
| 2003/0191398 | A1 | 10/2003 | Motx |
| 2004/0010197 | A1 | 1/2004 | Faupel |
| 2004/0033514 | A1 | 2/2004 | Rothschild |
| 2004/0186383 | A1 | 9/2004 | Rava et al. |
| 2004/0207625 | A1 | 10/2004 | Griffin |
| 2005/0052645 | A1 | 3/2005 | Stewart |
| 2005/0137180 | A1 | 6/2005 | Robinson et al. |
| 2005/0171436 | A1 * | 8/2005 | Clarke et al. ............ 600/476 |
| 2005/0228594 | A1 | 10/2005 | Pryce-Lewis et al. |
| 2005/0250091 | A1 | 11/2005 | Maier |
| 2005/0251116 | A1 | 11/2005 | Steinke et al. |
| 2005/0277816 | A1 | 12/2005 | Maier |
| 2006/0160134 | A1 | 7/2006 | Melker et al. |
| 2006/0177379 | A1 | 8/2006 | Asgari |
| 2006/0253261 | A1 | 11/2006 | Maier |
| 2007/0070343 | A1 | 3/2007 | Cohen |
| 2007/0078500 | A1 | 4/2007 | Ryan et al. |
| 2007/0127022 | A1 | 6/2007 | Cohen |
| 2007/0148697 | A1 | 6/2007 | Delaney et al. |
| 2007/0178067 | A1 | 8/2007 | Maier |
| 2007/0182959 | A1 | 8/2007 | Maier |
| 2007/0258894 | A1 | 11/2007 | Melker et al. |
| 2008/0228428 | A1 | 9/2008 | Balss et al. |
| 2009/0187108 | A1 | 7/2009 | Tang et al. |

FOREIGN PATENT DOCUMENTS

| | | |
|---|---|---|
| WO | 8902718 | 4/1989 |
| WO | 9215008 | 9/1992 |
| WO | WO9303672 | 4/1993 |
| WO | WO9730338 | 6/1997 |
| WO | WO02077587 | 10/2002 |
| WO | 02096366 | 12/2002 |
| WO | 03060444 | 7/2003 |
| WO | WO2004051242 | 6/2004 |
| WO | 2005060380 | 7/2005 |
| WO | 2005096429 | 10/2005 |
| WO | 2006069677 | 7/2006 |
| WO | 2007041542 | 4/2007 |
| WO | 2007086986 | 8/2007 |

OTHER PUBLICATIONS

Crow et al, "Noninvasive Detection of Genetic Instability in Cells from Secretion as a Marker of Prostate Cancer," European Journal of Internal Medicine, 2001. 12:17-19.

Leroy et al, "Canine Prostate Carcinomas Express Markers of Urogelial and Prostatic Differentiation," Vet. Pathol. (2004) 41:131-140.

Technology License Opportunity, "Hyperspectral Imaging for Cancer Detection," 2 pp (c) 2004 Science Applications International Corporation.

Miseo et al, "Developing a Chemical-Imaging Camera," The Industrial Physicist, Oct./Nov. 2003, 29-32.

Chen et al, "Proceedings of the National Science Council," ROC Part B: Life Science, 1996: 20(4): 123-130.

Huang et al, Int. J. Cancer, 2003. 107, 1047-1052.

Hawi et al, Caner Letters 1996, 110:35-40.

Redd, D. C.B. et al, Applied Spectroscopy, 1993, 47, 787-791.

Frank et al, Analytical Chemistry 1994, 6, 319-326.

Schaeberle et al, Analytical Chemistry, 1996, 68, 1829-1833.

Kline et al, Journal of Raman Spectroscopy, 1997, 28, 119-124.

Sijtsema et al, Applied Spectroscopy, 1998. 52, 348-355.

Colarusso et al, SPIE 1999, 3608, 139-145.

Beljebbar et al, SPIE, 1999, 3608, 175-184.

Morris et al, SPIE 2000, 3918, 2-8.

Nijssen et al, Journal of Investigative Dermatology, 2002, 119, 64-69.

Shafer-Peltier, K.E. et al, Journal of Cellular Biochemistry, Supplement 2002, 39, 125-137.

Koljenovis et al, Laboratory Investigation, 2002, 83, 1265-1277.

Ling et al, Applied Optics, 2002, 41. 6006-6017.

Uzunbajakava et al, Biopolymers 2003, 72. 1-9.

Uzunbajakava et al, SPIE 2003, 4963, 223-230.

Widaja et al, Applied Spectroscopy, 2003, 57, 1353-1362.

Van Manen et al, Journal of the American Chemical Society 2003, 125, 12112-12113.

Josi et al, SPIE 2004, 5325, 89-95.

Heinrich et al, Applied Physics Letters, 2004, 84, 816-818.

Maier et al, SPIE 2004, 5588, 98-105.

Stewart et al, "A Fast Method for Detecting Cryptosporidiurn Parvum Oocysts in Real World Samples," Advanced Biomedical and Clinical Diagnostic Systems III, SPIE, vol. 5692, 2005, pp. 341-350.

Maquelin et al, "Identification of Medically Relevant Microorganisms by Vibrational Spectroscopy," Journal of Microbiological Methods, Elsevier, Amsterdam, NL, vol. 51, No. 3, Nov. 1, 2002, pp. 255-271.

Extended European Search Report, PCT/US2006029187, Nov. 24, 2009.

Supplementary European Search Report, PCT/US03/00868, Oct. 8, 2010.

Written Opinion of the International Searching Authority, PCT/US2006/029187, Aug. 26, 2008.

International Preliminary Report on Patentability, PCT/US2006/029187, Mar. 1, 2011.

* cited by examiner

```
                                                                200
┌─────────────────────────────────────────────────────┐
│  illuminating a sample with substantially           │
│  monochromatic light to thereby produce Raman       │
│  scattered photons, wherein said sample comprises at│   210
│  least one of: a drug delivery device, a matrix     │
│  associated with a drug delivery device, a drug, and a│
│                      tissue;                        │
└─────────────────────────────────────────────────────┘
                          │
                          ▼
┌─────────────────────────────────────────────────────┐
│  assessing said Raman scattered photons to thereby  │
│     generate at least one spectroscopic data set    │
│        representative of said sample, wherein said  │
│  spectroscopic data set comprises at least one of: a│   220
│     Raman spectra of the sample and a spatially     │
│     accurate wavelength resolved Raman image        │
└─────────────────────────────────────────────────────┘
                          │
                          ▼
┌─────────────────────────────────────────────────────┐
│  evaluating said spectroscopic data set to thereby  │
│    identify at least one of: a drug delivery device, a│
│  matrix associated with a drug delivery device, a drug,│  230
│                   and a tissue.                     │
└─────────────────────────────────────────────────────┘
```

310 — illuminating a sample with substantially monochromatic light to thereby produce Raman scattered photons, wherein said sample comprises at least one of: arterial tissue and a drug-eluting stent;

320 — assessing said Raman scattered photons to thereby generate at least one spectroscopic data set representative of said sample, wherein said spectroscopic data set comprises at least one of: a Raman spectra of the sample and a spatially accurate wavelength resolved image of the 330 — evaluating said spectroscopic data set to thereby determine at least one of: an attribute of the arterial tissue and an attribute of the drug-eluting stent.

Figure 3

Figure 2: Raman dispersive spectrum of PLGA.

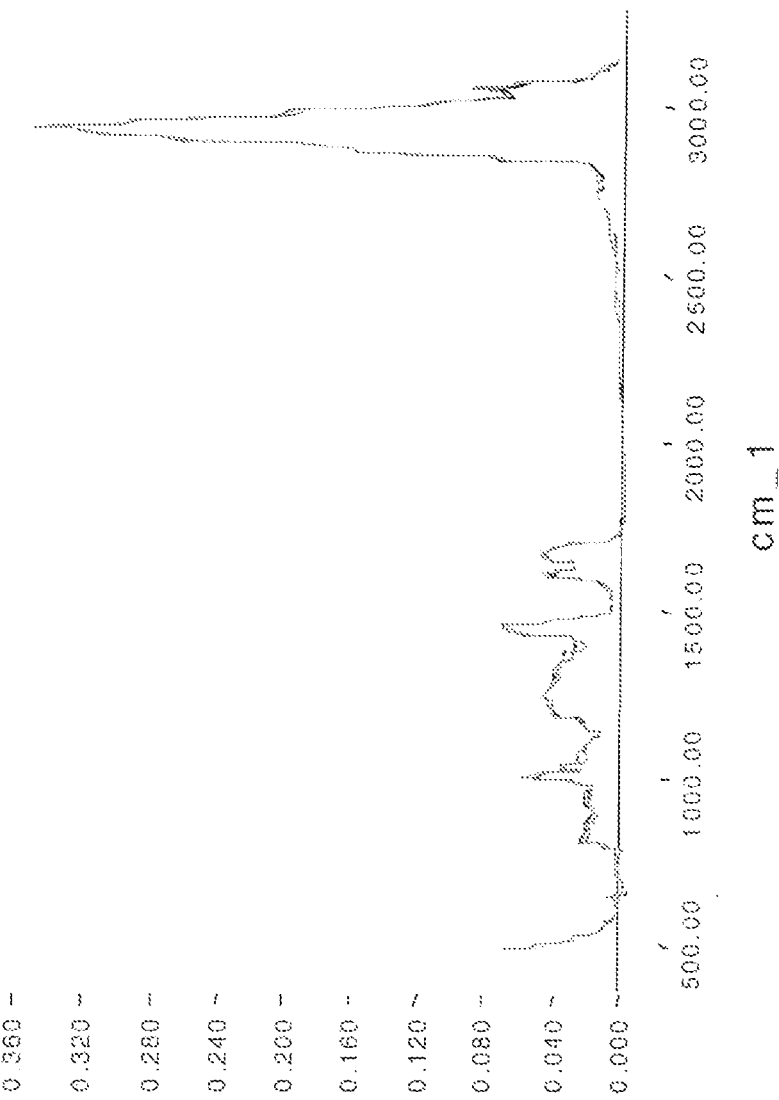
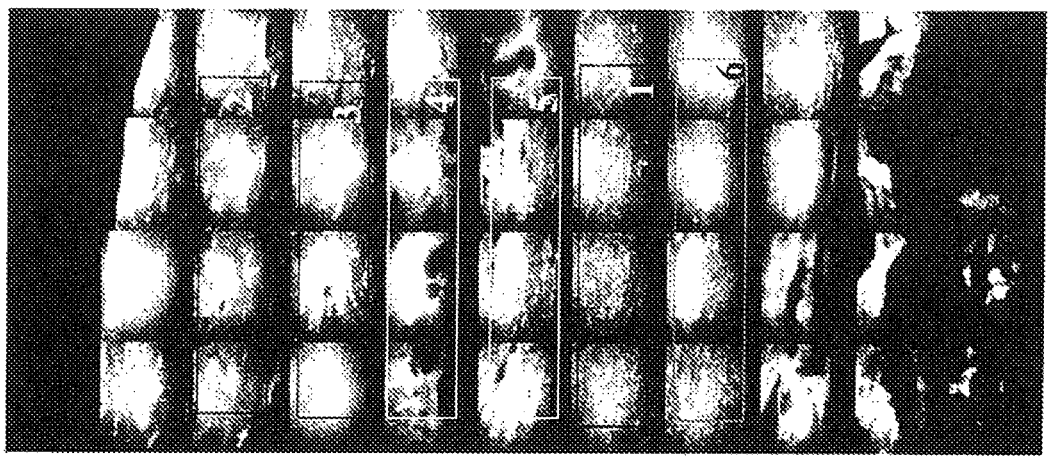
Figure 13

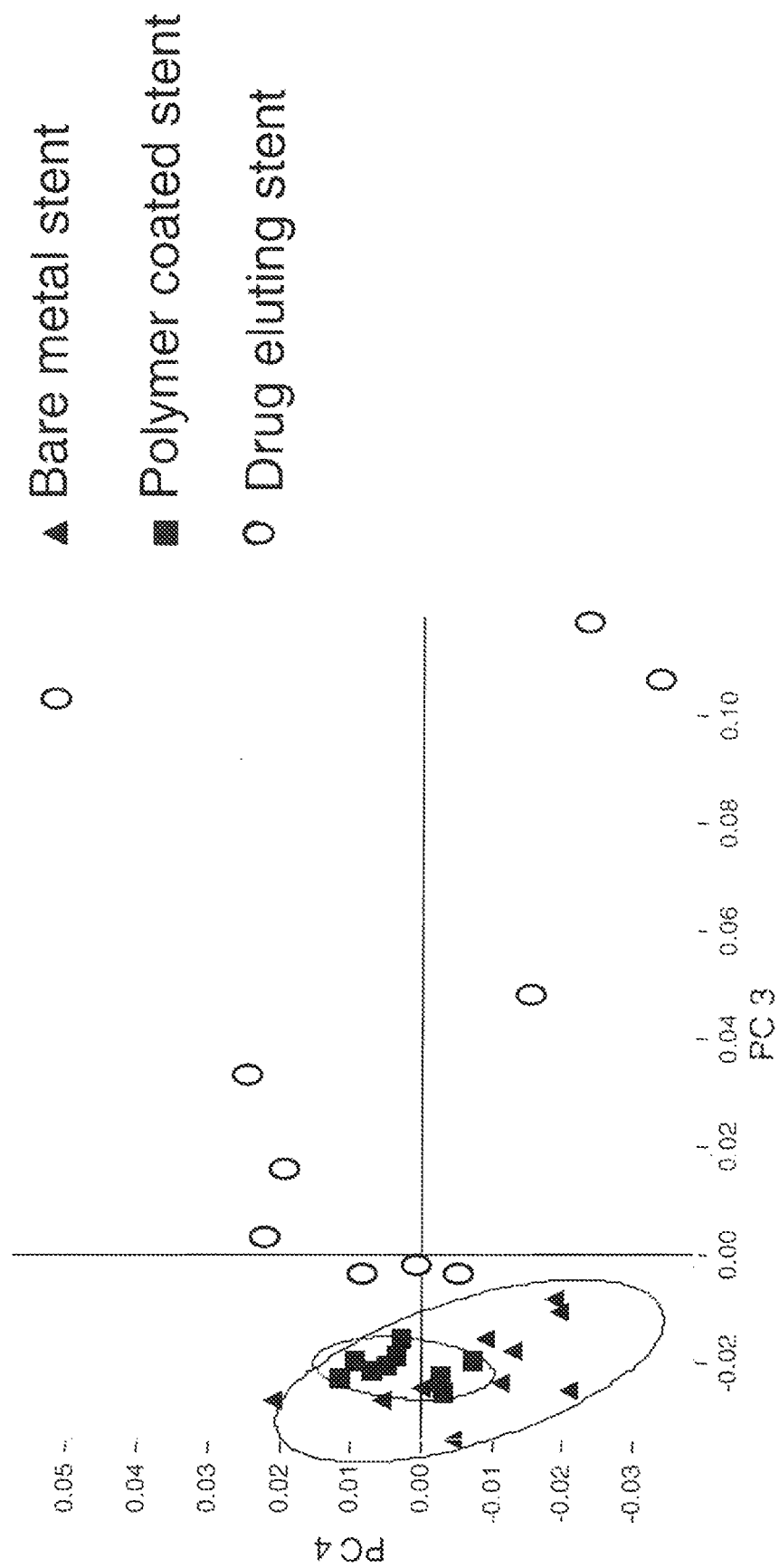

RAMAN CHEMICAL IMAGING OF IMPLANTABLE DRUG DELIVERY DEVICES

RELATED APPLICATIONS

This application claims priority to U.S. Provisional Application No. 61/188,351, filed on Aug. 8, 2008, entitled "Raman Chemical Imaging of Implantable Drug Delivery Devices" and to U.S. Provisional Application No. 61/026,538, filed on Feb. 6, 2009, entitled "Raman Chemical Imaging of Arterial Tissue".

BACKGROUND

Implantable drug delivery devices are a new type of medicinal therapy. After implantation, the devices release a drug at a predictable rate directly to the tissue that will benefit from treatment. Typically, the implantable drug delivery devices are made up of a pharmaceutical agent (active agent) coated with a biocompatible, biodegradable material called a matrix. The device may be implanted into the tissue where the drug is to act. With time, the drug can be released into the tissue by diffusion and/or biodegradation of the coating. This localizes the drug specifically to the tissue where it is necessary, having considerable advantages including control over the drug delivery and the ability to use drug formulations that cannot be delivered orally or by injection. The result is improved efficacy, reduced toxicity, and improved patient compliance and convenience.

The active agent can be any drug or pharmaceutical preparation; for example, an anti-cancer agent. Delivery of the anti-cancer drug specifically at the site of the cancer will reduce the potential side effects or damage to non-cancerous tissue. The coating of the implantable drug delivery device is usually a polymeric matrix that is composed of a poly-a-amino acid, which naturally occurs in humans. With time, the matrix will degrade in the body due to natural processes of the host. However, it is not mandatory that the matrix degrade in the host, and other biomaterials are possible. Common shapes of implantable drug delivery devices include but are not limited to microspheres and rods, among others.

There are different modes of action of implantable drug delivery devices, depending on the system. The most common implantable drug delivery device may work through controlled release mechanisms, environmentally responsive systems, or biodegradable systems. In a controlled release mechanism, a drug or other active agent diffuses out from the polymer that forms the device. The combinations of polymer matrices and bioactive agents chosen must allow for the drug to diffuse through the pores or macromolecular structure of the polymer upon introduction of the delivery system into the biological environment without inducing any change in the polymer itself. In an environmentally responsive system, the device is designed so that it is incapable of releasing its agent or agents until it is placed in an appropriate biological environment. An example of this is a hydrogel that swells when in contact with water or other bodily fluids. In biodegradable systems, the device degrades within the body as a result of natural biological processes. This eliminates the need to remove a drug delivery system after release of the active agent has been completed. The future directions of implantable drug delivery devices lie in the area of responsive delivery systems, where drugs or active agents will be delivered through implantable devices in response to a specific biological function.

One example of an implantable drug delivery device is a drug-eluting stent, which is used to prevent artery collapse. Coronary arteries are the network of arteries that provide blood flow to the heart tissue itself. The arteries deliver the oxygen and vital nutrients the heart needs to function properly. In youth, coronary arteries are smooth, elastic, hollow tubes through which blood can flow freely. As aging occurs, fat builds up on the walls of the coronary arteries, causing slight injury to the blood vessel walls. In an attempt to heal the injury, the cells of the blood vessel walls (endothelial cells) release chemicals that attract other substances traveling through the blood stream, such as inflammatory cells, proteins and calcium. The fat and other substances combine to form a material called plaque, which builds up until it eventually clogs and narrows the artery, a process called atherosclerosis. Coronary artery disease (CAD) is when the arteries of the heart become atherosclerotic, restricting bloodflow to the heart muscle itself.

If the heart does not get enough oxygen and nutrients due to reduced blood flow in the blocked arteries, one may experience chest pain called angina. When one or more of the coronary arteries are completely blocked, the result is a heart attack, which is injury to the heart muscle. Typically, most individuals with coronary heart disease might show no evidence of disease for decades as the disease progresses. There may be no indication of disease before the first onset of symptoms, which is often a sudden heart attack.

Interventional procedures such as balloon angioplasty and stent placement are common methods to treat CAD. These procedures are considered non-surgical because they are done by a cardiologist through a catheter inserted into a blood vessel, rather than by a surgeon. In the balloon angioplasty procedure, a small balloon at the tip of the catheter is inserted near the blocked or narrowed area of the coronary artery. When the balloon is inflated, the fatty plaque or blockage is compressed against the artery walls and the diameter of the blood vessel is widened (dilated) to increase blood flow to the heart. Sometimes after this procedures restenosis or artery collapse occurs, where the artery becomes reblocked. To overcome this, in most cases, balloon angioplasty is performed in combination with the placement of a stent. A stent is a small, metal, mesh tube that acts as a scaffold to provide support inside the coronary artery to prevent restenosis. A balloon catheter is used to insert the stent into the narrowed artery, and the stent stays in place permanently. The artery heals around the stent, somewhat diminishing restenosis.

Although stents seemed to prevent artery collapse, restenosis was still a problem leading to the development of drug-eluting stents. A drug-eluting stent is a normal metal stent that has been coated with a pharmacologic agent (drug) that is known to interfere with the process of restenosis. Drug-eluting stents contain a medication that is actively released at the stent implantation site. There are three major components to a drug-eluting stent: the bare metal stent itself, coating on the stent (typically polymetric) to deliver the drug to the arterial wall, and the drug itself.

Pharmaceutical companies who design drug delivery devices must be able to indicate efficaciousness of an implantable drug delivery device to the FDA. Some issues that must be addressed include the rate of drug delivery, the diffusion of the drug, the affect of the drug on a tissue, and the degradation of the matrix, among others. Companies that produce drug-eluting stents are interested in ascertaining how the stent (including drug and delivery-mechanism) affects the tissue. The current standard is for pathologists to study the tissue after placement of the stent. The pathologist looks at three main factors: histology, morphology, and morphometry. Histology is the study of thin sections of tissue. Pathologists will look at arterial tissue sections, stained with appropriate histological stain, to be able to visualize the vascular structure of the tissue. Such structures include the different layers of the artery: the neointima, internal elastic lamina (IEL), media, external lumina (EEL), and adventitia.

Morphology evaluates the nature of a cellular response in a qualitative fashion. Stent implantation elicits a well documented cellular, healing response. The significant characteristics of the cellular response to stents include: damage to vascular structures, presence of inflammation, foreign body reaction, and cellular and tissue types preset in the neo-intimal response.

Morphometry evaluates the vascular structures and reaction to the stent in a quantitative manner. The areas of the different regions (i.e. medical area, neointimal area) are calculated and compared.

Microscopy of the excised tissue can be used to study the implantable drug delivery devices. Although pathologists gain some insight into the cellular response, they are limited to only what they can see visually in the tissue or stained tissue. Finding the implanted drug delivery devices under a microscope can be tedious and time consuming. In addition, actual molecular analysis of the tissue, such as the presence of the drug, diffusion of the drug, biochemical composition of the tissue, changes in the tissue due to the drug, and identification of fluid and cellular components, still remain a challenge. Therefore, other analytical alternatives are necessary to aid the pathologist in evaluation of tissue.

As biology research and clinical medicine both move toward a more molecular level of understanding, there is a growing need for tools, which can evaluate biological samples with sensitivity to subtle molecular differences, such as in the case of a drug delivery device implanted into a tissue. Because biological processes in cells and tissues occur through localized chemical changes in specific cells or subcellular structures, a spatial resolution of molecular distinctions is very useful, if not necessary.

SUMMARY

This application relates generally to systems and methods for analyzing implantable drug delivery devices, including drug-eluting stents. The present disclosure provides for a method of detecting, measuring, and analyzing implantable drug delivery devices using Raman chemical imaging (RCI). The present disclosure also provides for analyzing tissue surrounding or in close proximity to such drug delivery devices to thereby determine the rate of drug delivery, the effect of the drug on a tissue, and the degradation of the matrix, among other attributes.

One analytical technique that is aptly suited for the study of implantable drug delivery devices is Raman spectroscopy. Raman spectroscopy is a tool traditionally used in chemical and material analysis. One reason Raman spectroscopy finds application in molecular analysis is the chemical specificity of Raman measurements. This specificity arises from the physical basis for the Raman scattering event. Raman scattering is inelastic scattering of photons off the vibrational states of molecules. Because the vibrational states of molecules depend on the inter-atomic bonds which are specific to a given molecular entity, the Roman scattering measurements are specific for specific chemicals. Since each component of the implantable drug delivery device is a distinct chemical, Raman spectroscopy can be used to spectrally identify the drug delivery device matrix, drug, and tissue.

One key aspect of maximizing information content obtained from Raman scattering measurements on cells and tissues is the ability to make measurements which are spatially localized within a given sample. This is important because the localization of certain molecules within regions of cells and tissues is critical to biological function, as is the case in drug delivery. Raman Chemical Imaging (RCI) is a method that can provide spectral and spatial information about the molecular environment of tissue that had been exposed to an implantable drug delivery device. The information provided by RCI, combined with histology, morphology, and morphometry, help pathologists and other researchers make informed evaluation of tissues and implantable drug delivery devices.

Regardless of the mode of action, active agent, or matrix, RCI is a valuable tool to study the major issues of the implantable drug delivery device. The polymer matrix and the drug itself can be spatially distinguished from the surrounding tissue using RCI because each compound will have its own unique Raman spectra. Therefore, depending on the implantable drug delivery device system, it is possible using RCI, to determine the diffusion of the drug into the tissue with time; changes to the tissue due to drug exposure; and degradation of the polymer matrix.

In particular, Raman chemical imaging is a method that holds potential for evaluating arterial tissue that has been exposed to a stent or a drug-eluting stent; or any interventional technique that is used to treat CAD.

BRIEF DESCRIPTION OF THE DRAWINGS

The accompanying drawings, which are included to provide further understanding of the disclosure and are incorporated in and constitute a part of this specification, illustrate embodiments of the disclosure and, together with the description, serve to explain the principles of the disclosure.

FIG. 2 is illustrative of one method of the present disclosure.

FIG. 3 is illustrative of one method of the present disclosure.

FIG. 13 is representative of the RCI of an atherosclerotic plaque in an artery;

FIG. 15 is a representative plot of the PCA of spectra (J3=2.14)

DETAILED DESCRIPTION

Reference will now be made in detail to the preferred embodiments of the present disclosure, examples of which are illustrated in the accompanying drawings. Wherever possible, the same reference numbers will be used throughout the drawings to refer to the same or like parts.

Figure 1:
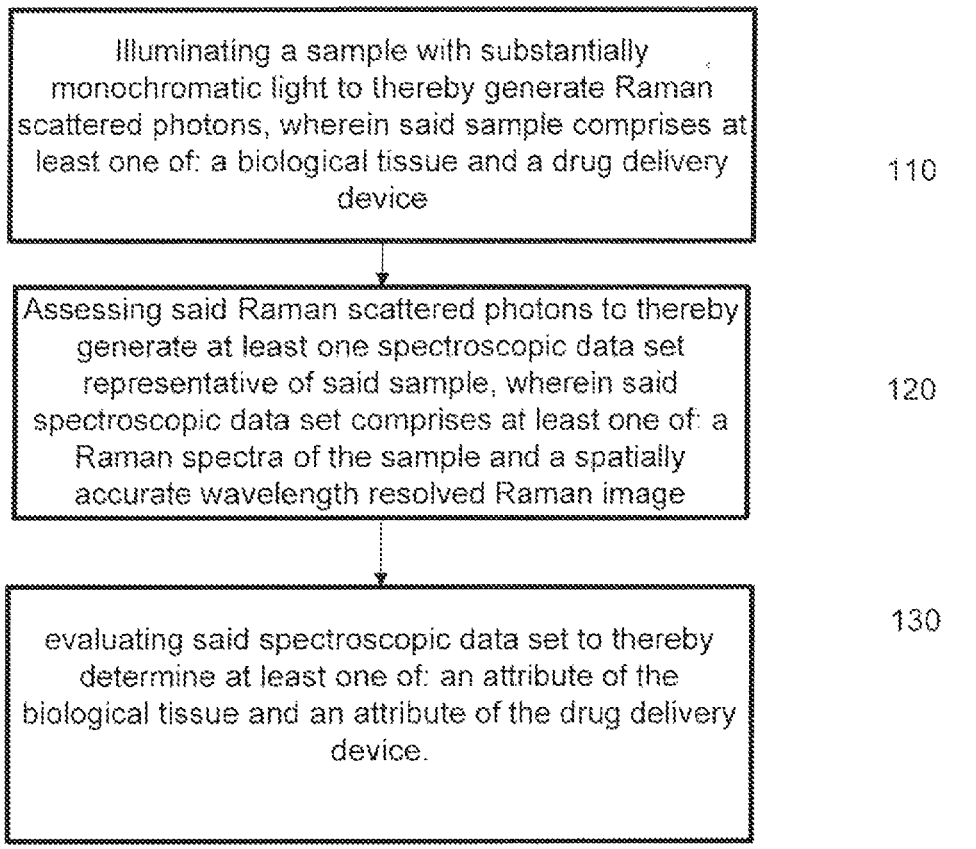
FIG. 1 is illustrative of one method of the present disclosure.

FIG. 1 is illustrative of one embodiment of the present disclosure. The method 100 comprises: illuminating a sample with substantially monochromatic light to thereby generate Raman scattered photons in step 110. In one embodiment, the sample comprises at least one of: a biological tissue and a drug delivery device. The Raman scattered photons are assessed in step 120 to thereby generate a spectroscopic data set. In one embodiment the spectroscopic data set comprises at least one of: a Raman spectra of the sample and a spatially accurate wavelength resolved Raman image of the sample. The spectroscopic data set is evaluated in step 130 to thereby determine at least one of: an attribute of the biological tissue and an attribute of the drug delivery device.

The attribute of the biological tissue may include but is not limited to: the presence of a drug in the tissue, the concentration of drug, the rate of drug delivery to the tissue, the biochemical composition of the tissue, and a change in the tissue due to the drug, among others. In one embodiment, the rate of drug delivery can be determined by the amount of drug present in a tissue at a specific time or at various points in time during a period of implantation.

The attribute of the drug delivery device may include but is not limited to: the size of the drug delivery device, the degradation of a matrix associated with the drug delivery device, the presence of a drug in the drug delivery device, the concentration of a drug in a drug delivery device, and the rate of diffusion of the drug, among others. In one embodiment, the rate of diffusion of a drug from a drug delivery device can be determined by the amount of drub present in a drug delivery device at a specific time or at various points in time during a period of implantation.

In one embodiment, the method further comprises assessing a visible microscopic image of the sample. Said assessing may include correlation of said visible image to the spectroscopic data set, and specifically to a spatially accurate wavelength resolved image, which may be a Raman image, of the sample. Said assessing may include evaluating morphology, morphometry, and histology of the sample.

FIG. 2 illustrates another embodiment of the present disclosure. The method 200 comprises: illuminating a sample with substantially monochromatic light to thereby produce Raman scattered photons wherein said sample comprises at least one of: a drug delivery device, a matrix associated with said drug delivery device, a drug, and a tissue in step 210. The Raman scattered photons are assessed in step 220 wherein said assessing comprises generating it least one spectroscopic data set representative of said sample. The spectroscopic data set may comprise at least one of: a Raman spectra of the sample and a spatially accurate wavelength resolved Raman image of the sample. The spectroscopic data set is evaluated in step 230 to thereby identify at least one of: a drug delivery device, a matrix associated with a drug delivery device, a drug, and a tissue.

In one embodiment, illustrated by FIG. 3, the drug delivery device is a drug-eluting stent and the tissue is arterial tissue. The method 300 comprises illuminating the sample in step 310 to thereby produce Raman scattered photons. In step 320, the Raman scattered photons are assessed to thereby generate at least one spectroscopic data set representative of said sample, wherein said spectroscopic data set comprises at least one of: a Raman spectra of the sample and a spatially accurate wavelength resolved Raman image of the sample. In step 330 the spectroscopic data set is evaluated to thereby determine at least one of: an attribute of the arterial tissue and an attribute of the drug-eluting stent. In one embodiment, a matrix associated with the drug delivery device is a polymer matrix. In one embodiment, the method further comprises assessing a visible microscopic image of the sample. Said assessing may include correlation of said visible image to the spectroscopic data set, and specifically to a spatially accurate wavelength resolved image, which may be a Raman image, of the sample. Said assessing may include evaluating morphology, morphometry, and histology of the sample.

In one embodiment, a reference data base is provided. The reference data base may comprise a plurality of reference data sets wherein each reference data set is representative of a known sample. The plurality of reference data sets may comprise but are not limited to: a plurality of reference Raman spectra, a plurality of reference spatially accurate wavelength resolved Raman images, a plurality of reference fluorescence spectra, a plurality of reference spatially accurate wavelength resolved fluorescence images, a plurality of reference infrared spectra, a plurality of reference spatially accurate wavelength resolved infrared images, a plurality of reference ultraviolet spectra, a plurality of reference spatially accurate wavelength resolved ultraviolet images, a plurality of reference visible spectra, a plurality of reference spatially accurate wavelength resolved visible images, and combinations thereof.

Figure 4:
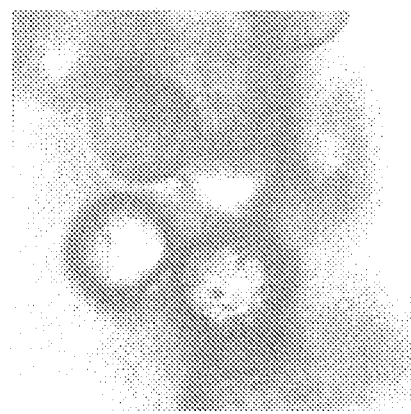
FIG. 4 is illustrative of a brightfield reflectance (BFR) image of a PLGA microsphere before implantation.
Figure 5:
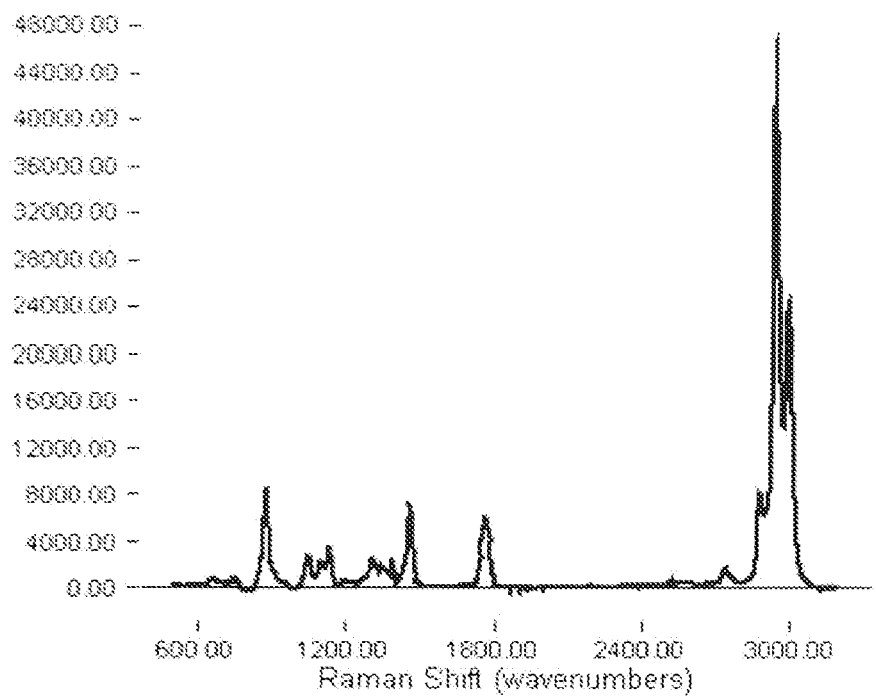
FIG. 5 is illustrative of the Raman dispersive spectrum of PLGA.

Raman chemical imaging holds potential for the analysis of implantable drug delivery devices. In FIG. 4, poly-lactic glycolic acid (PLGA) microspheres were implanted into murine kidneys. Initially, a sampling of the PLGA microspheres was analyzed by brightfield reflectance (BFR) before implantation. FIG. 4 shows the BFR image of a sample of microspheres. The average diameter of such a microsphere is 11.7 mm. FIG. 5 shows the Raman dispersive spectrum of PLGA.

Figures 6A, 6B, 6C:
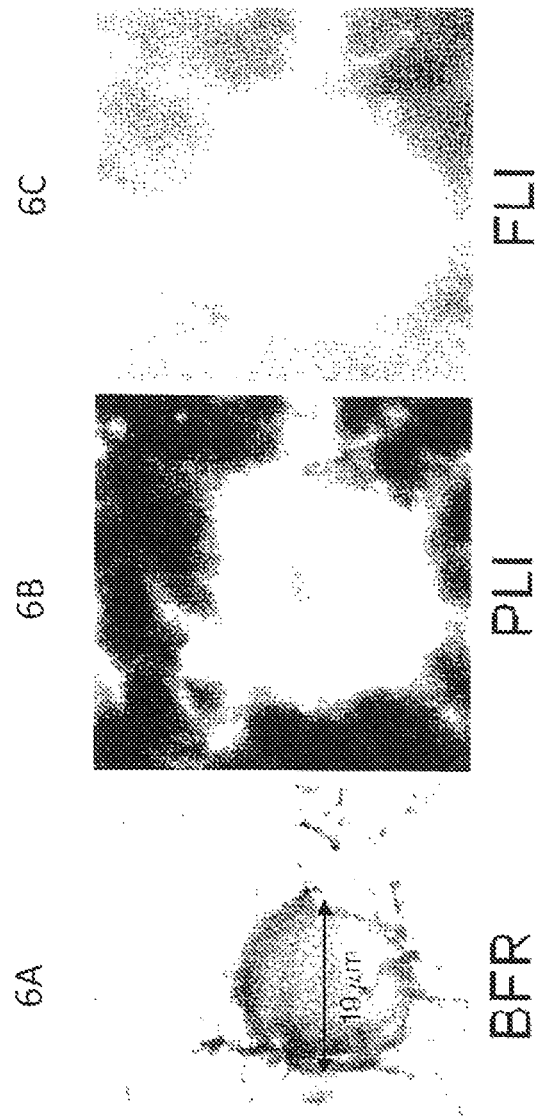
FIG. 6A is representative of the BFR of kidney tissue section containing PLGA microsphere.
FIG. 6B is representative of a polarized light image (PLI) of kidney tissue containing a PLGA microsphere.
FIG. 6C is representative of a fluorescence light image (FLI) of kidney tissue containing a PLGA microsphere.

Histological sections of murine kidney containing PLGA microspheres were examined using RCI. In one embodiment, different modalities of visual images may be obtained before the RCI. The visual modalities include BFR, polarized light image (PLI), and fluorescence light image (FLI). FIGS. 6A, 6B, and 6C show the BFR (FIG. 6A), PLI (FIG. 6B), and FLI (FIG. 6C) of kidney tissue section containing a PLGA microsphere.

Figures 7A, 7B:
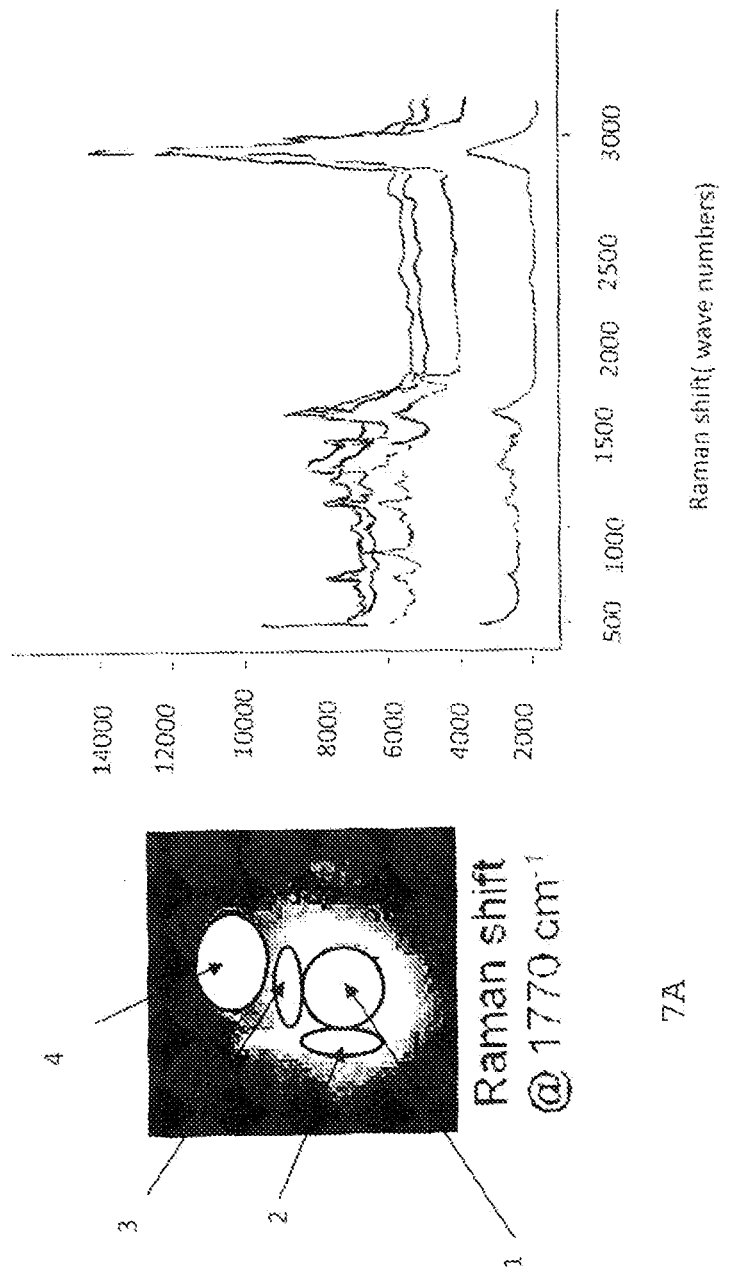
FIGS. 7A and 7B illustrate the RCI and Raman spectra of the microsphere in the kidney.

FIGS. 7A and 7B show the RCI and Raman spectra of the microsphere in the kidney section. A few important notes can be made about the image. First, the spectrum of the PLGA microsphere (labeled as feature 1) and the spectrum of the surrounding kidney tissue (labeled as feature 4) are distinct. The peaks at 872 and 1770 $cm^{-1}$ are specific for PLGA (FIG. 5). Second, the area directly around the microsphere (labeled as features 2 and 3, respectively), which appear to be part of the microsphere (FIG. 6), is actually spectrally distinct from both the kidney tissue and the microsphere. This area may be tissue reaction to the foreign material or degrading PLGA. Regardless of the reason for the difference, RCI is sensitive enough to defect the spectroscopic differences. Third, the BFR image (FIG. 6A) indicates that the size of the microsphere (19 mm). This is larger than the average size expected of 11.7 mm. The RCI, however, provides a measurement much closer to that expected, indicating that the size of the microsphere is 12 mm. It is evident, therefore, that RCI is more sensitive than other microscope modalities in detecting and measuring implanted drug delivery devices.

It is important to note that RCI is sensitive enough to distinguish changes in the tissue due to the implanted PLGA (spectra 2 and 3, and ROIs 2 and 3 in FIG. 7A). The presence of the implant likely caused the changes in the tissue, which is reflected in the spectral differences. When a drug delivery device is implanted into tissue, there will be changes in the tissue due to the drug and/or the implant. Even if the drug itself is not detectable by RCI, changes in the tissue reflected in spectral differences due to exposure to the drug will be measurable. RCI is more useful than visible microscopy and can be used to find the implanted microspheres in tissue. A detection algorithm can be created to search an entire section of kidney for microspheres. Then those regions of interest (ROI) can be relocated for further study. The detection or targeting algorithm, where the tissue section is imaged just over a spectral range that will specifically identify the implanted drug delivery device, will be much faster than visibly searching the tissue under high magnification. In addition, chemometric techniques, such as spectral mixture resolution and principal component analysis (PCA), will be useful in the targeting algorithms. Other chemometric techniques that may be used include any such technique known in the art including but not limited to one or more of the following: minimum noise fraction, linear discriminate analysis, Mahalanobis distance, partial least squares discriminate analysis, Euclidean distance, partial least squares regression, support vector machines, maximum likelihood estimation, Bayesian classification, neutral networks, hidden markov models, and k-nearest neighbors, among others.

Another point in favor of targeted searching using RCI is the fact that visibly identifying microspheres may not provide enough information to identify them as an implanted device. As shown above, the BFR image was not able to show the difference between the reacted tissue around the microsphere and the microsphere itself. Possibly, the PLGA microsphere might have been dismissed as not being the drug delivery device because it was too large. Furthermore, visual identification of a microsphere using a microscope cannot confirm the composition of the microsphere.

Figures 8A, 8B, 8C:
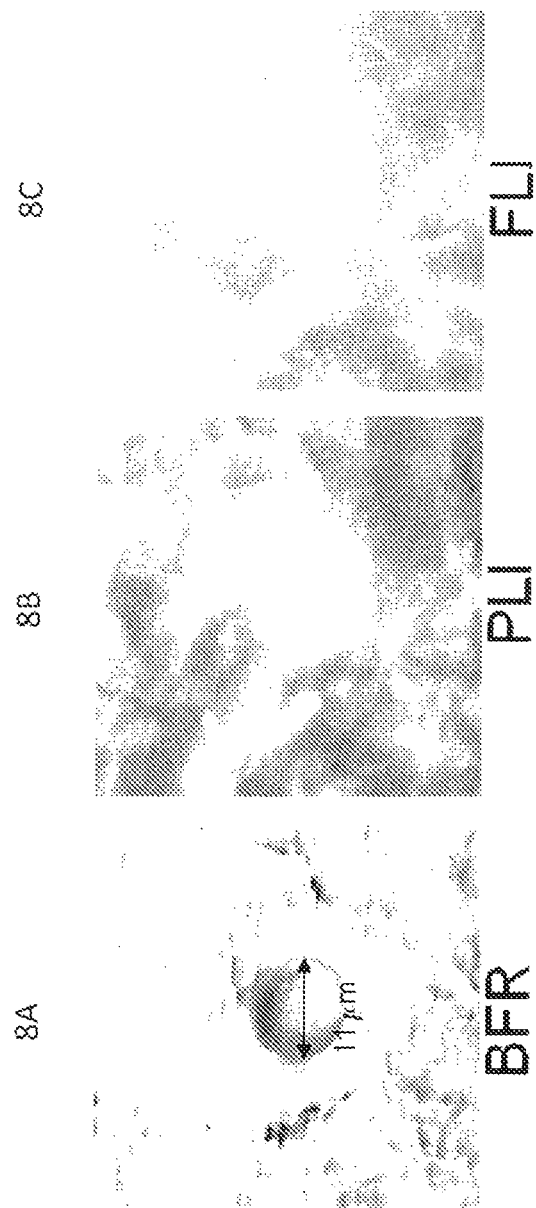
FIGS. 8A-8C illustrate murine kidney sections containing a microsphere at 50× magnification.

In FIGS. 8A, 8B, and 8C, a second microsphere was identified in the same kidney section as the as the PLGA microsphere shown in FIGS. 6A, 6B, 6C and 7A, 7B.

Figures 9A, 9B:
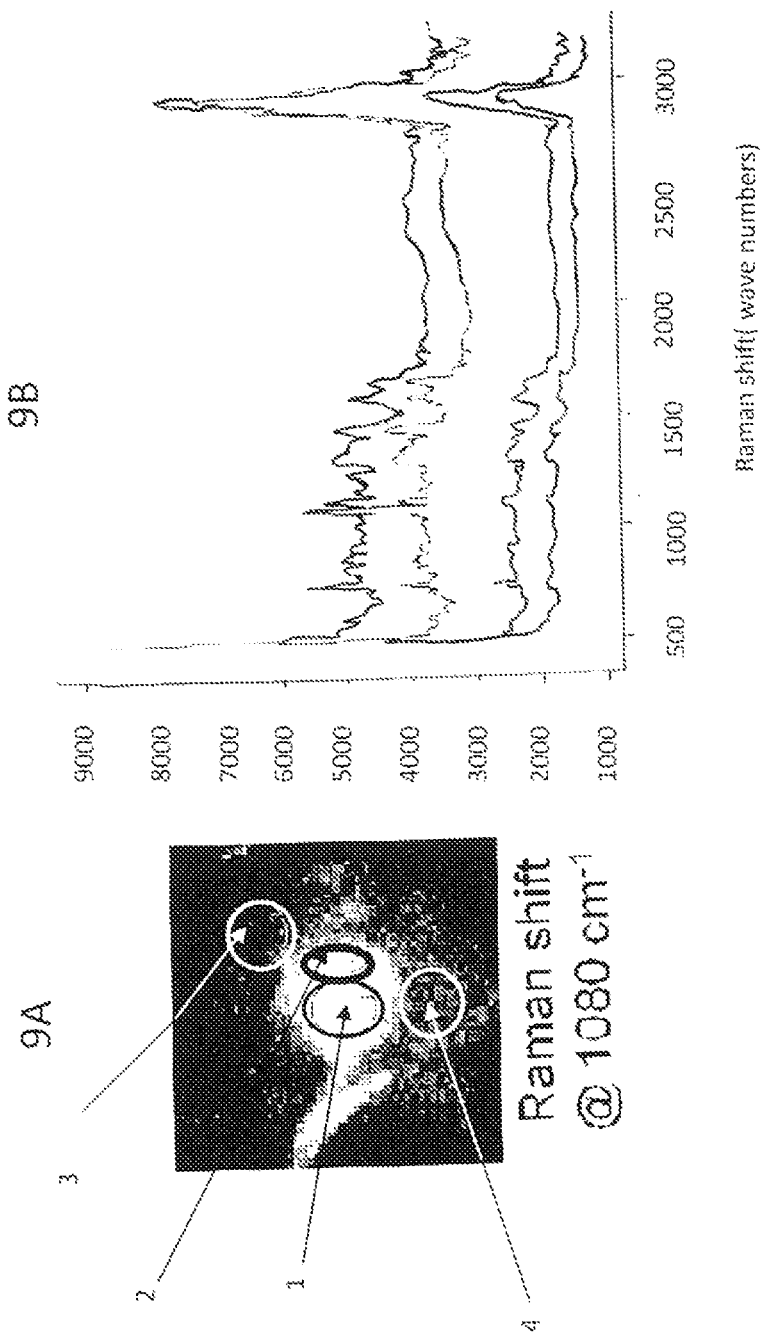
FIGS. 9A and 9B illustrate Raman chemical images at 1080 $cm^{-1}$ and the average spectrum of the indicated regions of the image.

According to the visible microscopic modalities, the size of the microsphere is 11 mm, which is the expected size of the PLGA microsphere. However, the RCI, shown in FIG. 9A, indicates that the spectrum (FIG. 9B) of the microsphere is not that of PLGA. The peak at 1080 cm-1 in the spectrum (spectra 1) of the microsphere, and the absence of peaks it 872 and 1770 cm$^{-1}$, indicates that the composition of the microsphere is not that of PLGA. After a library search of dispersive spectra, the microsphere in FIG. 9A was identified as calcium carbonate. This is not unusual because mice have crystals of calcium carbonate in their kidneys to help regulate urine. Nonetheless, the example demonstrates the need for a powerful tool such as RCI in the study of implantable drug delivery devices.

Figure 10:
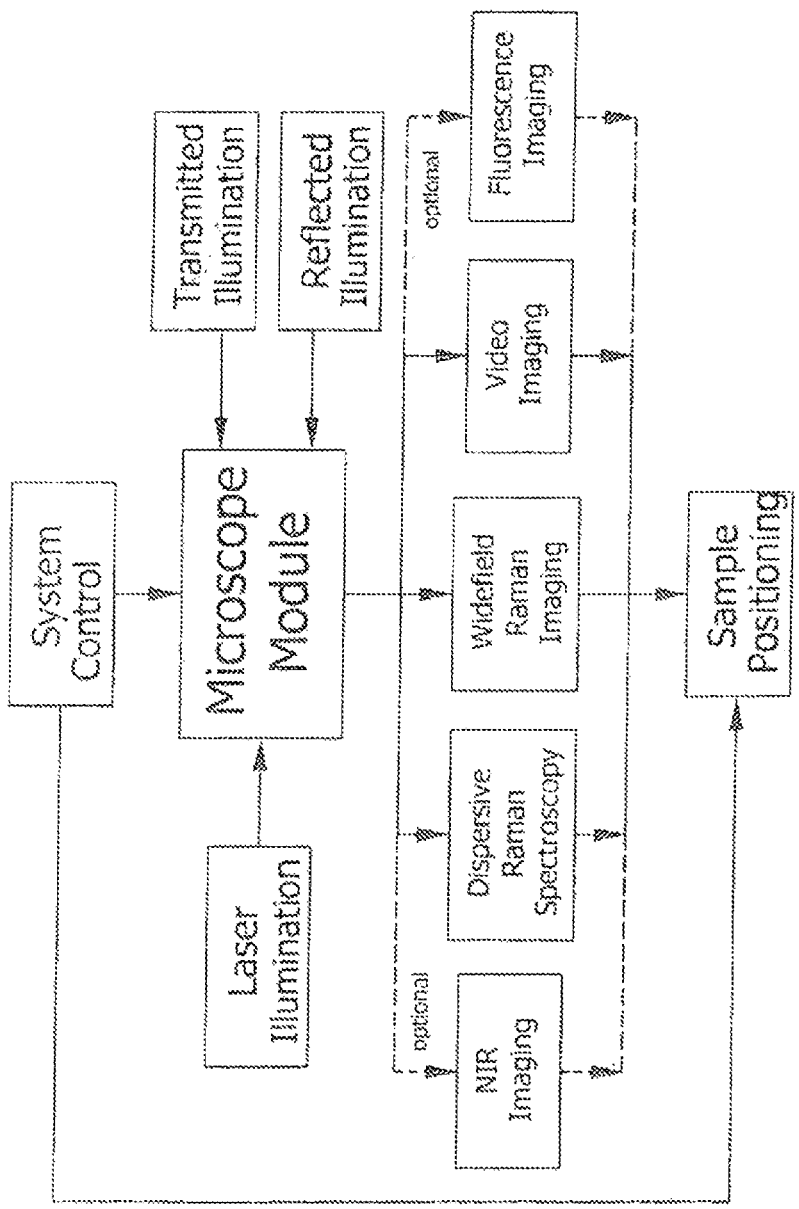
FIG. 10 is a schematic layout of a system of the present disclosure.

FIG. 10 illustrates a schematic layout of an exemplary ChemImage Falcon II™ Raman chemical imaging system which may be used to collect various Raman spectra and Raman chemical images as depicted herein.

In one embodiment of the present disclosure. Raman chemical imaging can be applied the analysis of arterial tissues. In another embodiment, different modalities of visual images can be obtained before obtaining the Raman chemical image of arterial tissue. The different modalities may include brightfield reflectance (BFR), polarized light image (PLI), and fluorescence light image (FLI).

One embodiment of the present disclosure provides for a method comprising: illuminating a sample with substantially monochromatic light to thereby produce Raman scattered photons wherein said sample comprises at least one of: arterial tissue and a drug-eluting stent. The Raman scattered photons are assessed wherein said assessing comprises generating at least one spectroscopic data set wherein said spectroscopic data set comprises at least one of: a Raman spectra of the sample an a spatially accurate wavelength resolved Raman image of the sample. The spectroscopic data set is evaluated to determine at least one of: an attribute of the arterial tissue and an attribute of the drug-eluting stent.

In one embodiment the attribute of the arterial tissue may include but is not limited to: the presence of a drug in the arterial tissue, the concentration of a drug in the arterial tissue, the rate of delivery of a drug to the arterial tissue, the biochemical composition of the arterial tissue, and a change in the arterial tissue due to the presence of a drug, among others. In one embodiment, the rate of drug delivery can be determined by the amount of drug present in the arterial tissue at a specific time or at various points in time during a period of implantation.

In one embodiment, the attribute of the drug-eluting stent can include but is not limited to: the size of the drug-eluting stent, the degradation of a coating associated with the drug-eluting stent, the presence of a drug in the drug-eluting stent, the concentration of a drug in a drug-eluting stent, and the rate of diffusion of a drug, among others. In one embodiment, the rate of diffusion of a drug can be determined by the amount of drug present in the drug-eluting stent at a specific time or at various points in time during a period of implantation.

In one embodiment, the method further comprises assessing a visible microscopic image of the sample. Said assessing may include correlation of said visible image to the spectroscopic data set, and specifically to a spatially accurate wavelength resolved image, which may be a Raman image, of the sample. Said assessing may include evaluating morphology, morphometry, and histology of the sample.

In one embodiment, the arterial tissue further comprises para-strut amorphous material. This material can be analyzed to identify at least one of: protein present in the material, fluid present in the material, and cellular components present in the material, among other constituent materials. The protein may comprise fibrin or other proteins and the fluid and cellular components may be indicative of an inflammatory response.

Figure 11:
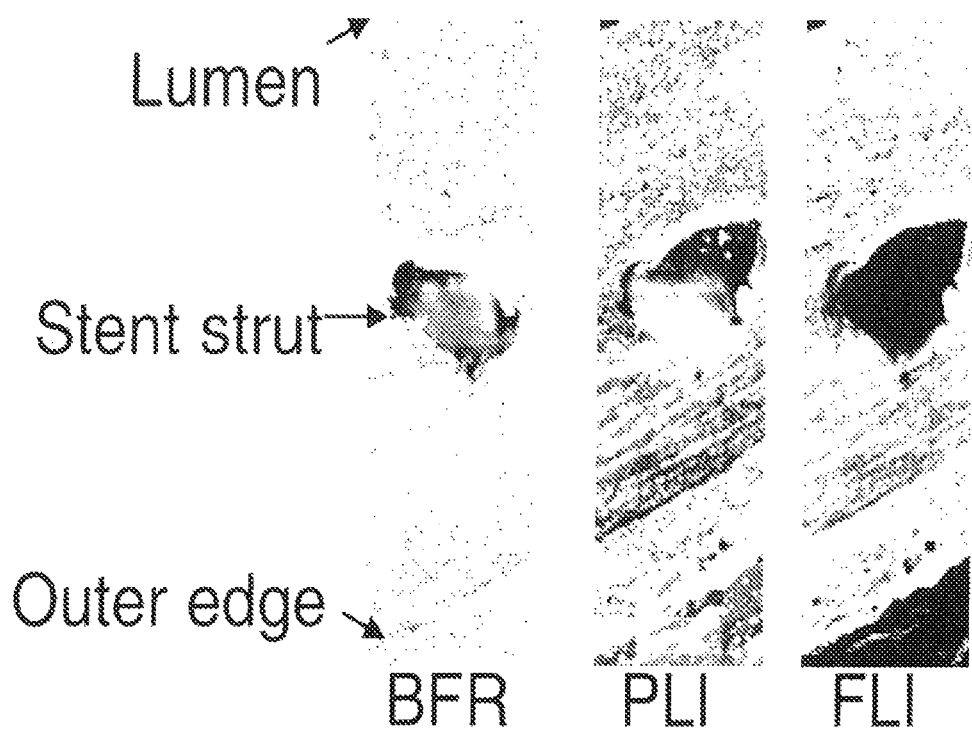
FIG. 11 is representative of the BFR, PLI, and FLI of an arterial segment containing a stent strut.
Figure 12:
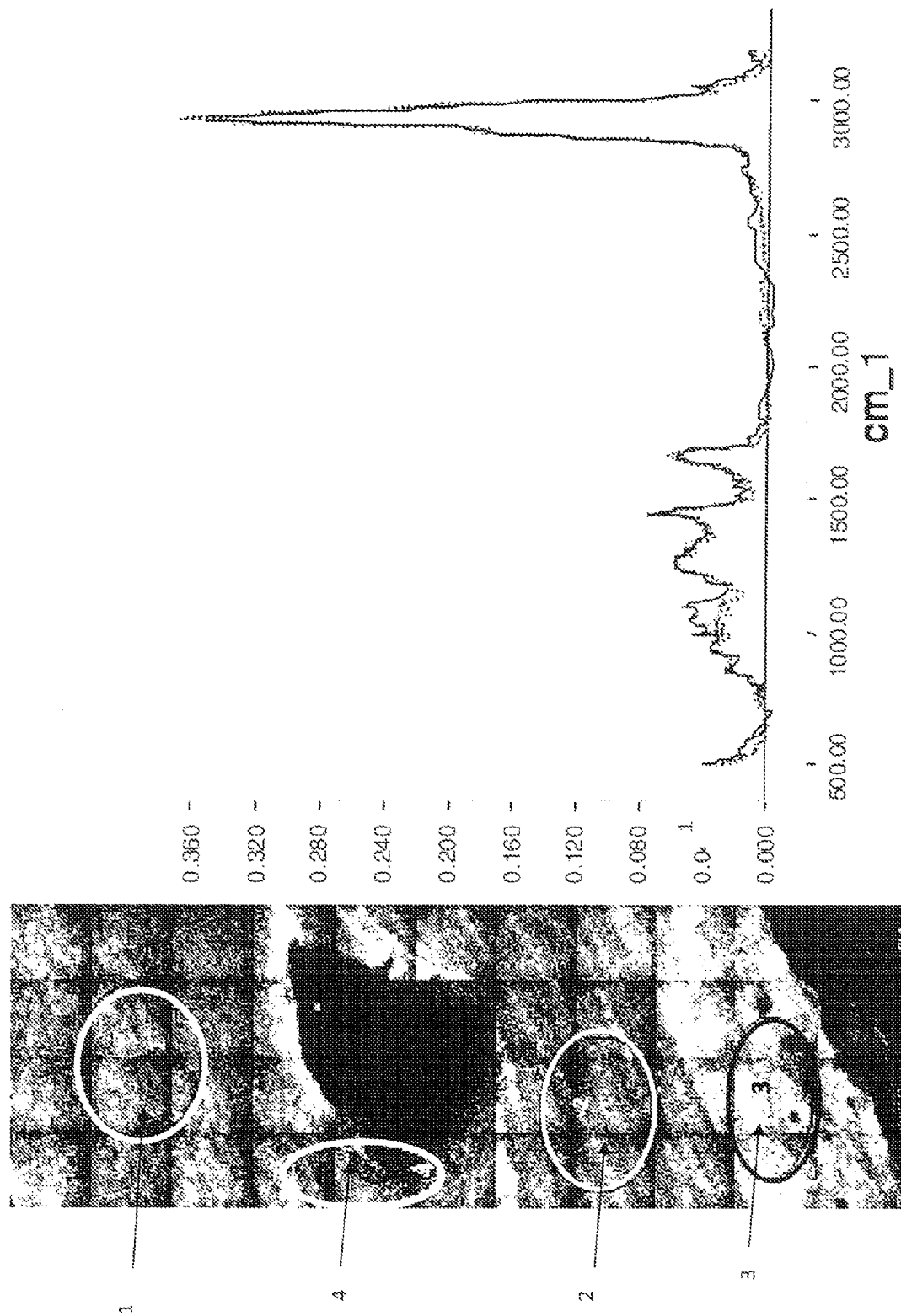
FIG. 12 is representative of the RCI at the Raman shift of 2930 $cm^{-1}$ and associated spectra of the indicated regions.

FIG. 11 is representative of the BFR, PLI, and FLI of an arterial segment containing a bare metal stent strut. The corresponding RCI is shown in FIG. 12, which shows the Raman shift at 2930 cm$^{-1}$ along with spectra of the circled regions of the different vascular layers of the artery. It is noted here that all Raman chemical images or Raman spectra depicted herein where obtained using FALCON II™ Raman chemical imaging system from ChemImage Corporation, Pittsburgh, Pa., USA.

Circled region 1 is the neointima, or the new arterial tissue that grew around the stent; circled region 2 is the media; and circled region 3 is in the adventitia. The spectra of the three different regions of the arterial segment are distinct; although on quick visual inspection, the spectra of the neointima and media seem more similar than that of the adventitia. This fact is not unexpected since the main cell type in both the neointima and media are the same—i.e., smooth muscle cells (SMC). This simple example illustrates that RCI provides useful information to help evaluate tissue.

Along with the vascular structures and arterial layers, pathologists are interested in examining para-strut amorphous material (PAM) that they encounter when examining arterial tissues containing stents. It may be desirable to find PAMs in a better way and to identify 1) fibrin and other proteins, and 2) fluid and cellular components of the inflammatory response contained within the PAMs. In FIG. 12, the circled region 4 is a PAM and the associated spectra are different from the other layers of the artery.

In another embodiment, RCI can be used to evaluate an arterial segment damaged by an atherosclerotic plaque. Sometimes when an artery is damaged, the tissue is replaced by scar tissue (fibroblasts, extracellular matrix) and will lose the differentiation of the arterial layers. FIG. 13 shows an RCI of an arterial segment damaged by an atherosclerotic plaque. It is observed from FIG. 13 that there is very little difference in the spectra of the selected regions of interest. Thus, spectral evidence of such lack of differentiation (of arterial layers) through RCI hold potential for helping a pathologist identify regions of damaged tissue that do not appeal visibly different by other techniques.

Figure 14:
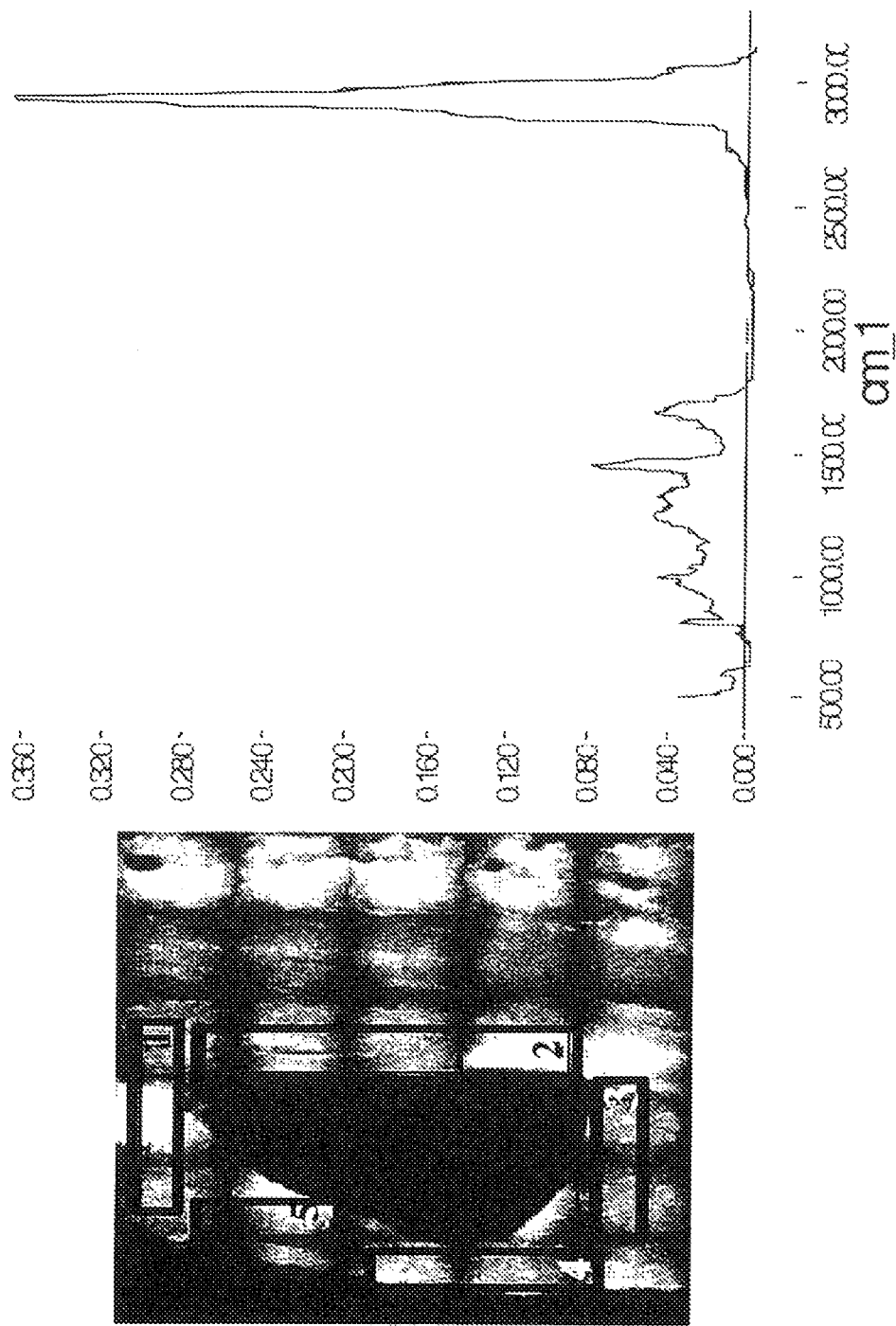
FIG. 14 is illustrative of collecting average Raman spectra of tissue around stent hole of a polymer coated stent.

Stent companies may be interested in whether the drug from a drug eluting stent causes any reaction or change in the tissue; especially when the stent has compounds present, such as the polymer coating on the stent. Pathologists at this time are having trouble proving that polymer coatings on stents do not cause adverse reaction in tissue, and also proving that drugs affect the tissue. To assist pathologists with these issues, RCI holds potential for imaging of 1) an arterial segment containing a bare metal stent and 2) an arterial segment containing a polymer coated stent. In one embodiment, spectra can be collected from regions around the stent hole for both tissues, as represented in FIG. 14.

In one embodiment, the spectra from the tissue containing the bare metal stent and tissue containing the polymer coated stent can be compared using one or more chemometric techniques. Said chemometric technique can be any known in the art including Mahalanobis distance and principle component analysis. In one embodiment, Principle Component Analysis is used. PCA is a multivariate data analysis technique which can be used to analyze the many Raman spectra associated with Raman image of the arterial tissue. The Raman spectra of different regions of the tissue (FIG. 14) are all very similar because the spectra are related to the same tissue building blocks (proteins, lipids, DNA); however, within these similar spectra, there may be some finite number of independent variations occurring in the spectral data. Preferably, the largest variations in the spectral data of a spectrum would be the changes in the spectrum due to different concentrations of biological molecules that make up cells/tissues, and not due to instrument variation. It is possible to calculate a set of "variation spectra" that represent changes in the Raman spectra (of biological molecules) at many or all wavelengths in the spectra. In one embodiment, "variation spectra" could be used instead of the spectral data for comparison. There should be fewer common variations amongst the data than the number of spectra. Although, since they come from the original data, the "variation spectra" retain the interrelationship of the original spectra. PCA is mathematically defined as an orthogonal linear transformation that transforms the data to a new coordinate system such that the greatest variance by any projection of the data comes to lie on the first coordinate (called the first principle component or first PC), the second greatest variance on the second coordinate (second PC), and so on.

Once the data is reduced, one can visualize the data by plotting different PC scores. The resulting plots are called scatter plots. The data points within a scatter plot represent the spectra and will cluster in PC space (coordinate system based on PC) according to similarities in spectral characteristics.

In one embodiment, Mahalanobis distance is used to measure the clustering of data points. The method is useful in determining the similarity of an unknown sample (test point) to an established clustered set, or ellipse, in PC space. The Mahalanobis distance is measured as the distance from one test point to the center of mass of the ellipsoid divided by the width of the ellipsoid in the direction of the test point. Therefore, it is based on both the size (determined from the standard deviation) and the shape of the ellipse (determined from the covariance, or how two groups vary with one another). The J3 value is indicative of the separation of the data.

In one embodiment, PCA and Mahalanobis distance are combined, providing a methodology that not only determines variation patterns within complex data sets, but also provides a way to measure and classify unknown data points to these known groups. Thus a classification system is created for samples that exhibit minor differences spectroscopically.

FIG. 15 depicts the results of chemometric analysis of exemplary spectra obtained from arterial tissue containing a bare metal stent, arterial tissue containing a drug eluting stent, and an arterial tissue containing drug eluting stent. The clustering of spectra form the tissue with the bare metal stent and the tissue from the polymer coated stent indicates that the spectra from these tissues are very similar. Conversely, the spectra from the tissue with the drug eluting stent are separate from the other spectra, indicating that such tissue is less similar to the other two samples; and the data are also more scattered. The scattering indicates that the spectra from the tissue with the drug eluting stent are variable. This may indicate that there may be variations in drug-cell interactions within the tissue. Chemometric analyses like the above may be useful to help pathologists distinguish the different biochemical environments within tissues after different treatments.

Classification models based on the data acquired by Raman spectroscopy and RCI and evaluated by chemometric techniques can be used to evaluate relevant biological changes in cells and tissues. In this case, the relevant biological change is that of arterial tissue being exposed to a drug; however, models for other metabolic changes in cells are also possible. A general application of being able to detect small changes in cells or tissues and the creation of models to classify the changes is in the detection and treatment of a disease. Classification models can be created of different metabolic processes within disease states using Raman spectroscopy and RCI to detect disease. Cell samples can then be evaluated using the classification models to ascertain and describe the disease state. Then, classification models can be treated cells. This can be further expanded to determining personalized drug treatments for individual patients suffering with a disease. More sophisticated classification models may be developed based on the goal of improving the sensitivity and specificity of the model classification in a given biological problem.

Raman spectroscopy and RCI are reagentless tools, which can be used to measure biologically relevant changes in cellular systems because of their ability, for example, to spectrally capture drug-cell interactions. These metabolic classification models show promise in the detection of disease states and in the selection of the best course of treatment for a specific disease, like CAD, from personalized drug treatments to the elimination of unwanted side effects. Raman spectra and RCI of a cell or tissue from a treated portion may be collected at different stages of the treatment to monitor the progress of the treatment.

In one embodiment of, the systems and methods provided for herein are performed in a laboratory environment. In another embodiment, the systems and methods provided for herein are performed in a clinical setting.

The present disclosure may be embodied in other specific forms without departing from the spirit or essential attributes of the disclosure. Accordingly, reference should be made to the appended claims, rather than the foregoing specification, as indicating the scope of the disclosure. Although the foregoing description is directed to the preferred embodiments of the disclosure, it is noted that other variations and modification will be apparent to those skilled in the art, and may be made without departing from the spirit or scope of the disclosure.

What is claimed is:

1. A method comprising:
   illuminating a biological tissue sample using wide-field illumination comprising a drug delivery device to generate interacted photons;
   assessing the interacted photons to generate at least one spatially accurate wavelength resolved Raman chemical image; and
   analyzing the spatially accurate wavelength resolved Raman chemical image to evaluate the drug delivery device, wherein analyzing further comprises comparing the image to at least one reference data set.

2. The method of claim 1 wherein comparing the spatially accurate wavelength resolved Raman image to at least one reference data set further comprises applying one or more chemometric techniques.

3. The method of claim 2 wherein the chemometric technique is selected from the group consisting of: principle component analysis, minimum noise fraction, linear discriminate analysis, Mahalanobis distance, partial least squares discriminate analysis, Euclidean distance, partial least squares regression, support vector machines, maximum likelihood estimation, Bayesian classification, neutral networks, hidden markov models, and k-nearest neighbors, and combinations thereof.

4. The method of claim 1 wherein the drug delivery device further comprises at least one of: a controlled release drug delivery device, an environmentally responsive drug delivery device, a biodegradable drug delivery device, a responsive drug delivery device, and combinations thereof.

5. The method of claim 1 wherein the drug delivery device further comprises a drug-eluting stent.

6. The method of claim 1 wherein the biological tissue sample further comprises arterial tissue sample.

7. The method of claim 1 wherein the biological tissue sample comprises arterial tissue and the drug delivery device comprises drug-eluting stent, further comprising detecting para-strut amorphous material in the arterial tissue.

8. The method of claim 7 farther comprising assessing the para-strut amorphous material to thereby identity at least one of: fibrin, a protein, fluid, a cell, a cellular component, and combinations thereof.

9. The method of claim 1 wherein evaluating the drug delivery device further comprises distinguishing between a matrix of the drug delivery device and at least one drug associated with the drug delivery device.

10. The method of claim 1 wherein evaluating the drug delivery device further comprises distinguishing between a biological tissue in contact with the drug delivery device and a matrix of the drug delivery device.

11. The method of claim 1 wherein evaluating the drug delivery device further comprises assessing the biological tissue in contact with the drug delivery device.

12. The method of claim 11 wherein assessing the biological tissue further comprises determining the presence of a drug associated with the drug delivery device in the biological tissue.

13. The method of claim 11 wherein assessing the biological tissue further comprises determining a concentration of a drug associated with the drug delivery device in the biological tissue.

14. The method of claim 11 wherein assessing the biological tissue further comprises measuring the rate of diffusion of a drug associated with the drug delivery device into the biological tissue.

15. The method of claim 11 wherein assessing the biological tissue further comprises measuring a change in the molecular composition of the biological tissue in response to a drug associated with the drug delivery device.

16. The method of claim 1 wherein evaluating the drug delivery device further comprises measuring degradation of a matrix associated with the drug delivery device.

17. The method of claim 1 wherein evaluating the drug delivery device further comprises measuring the size of the drug delivery device.

18. The method of claim 1 further comprising:
   generating a visible image representative of the biological tissue sample; and
   assessing the visible image using at least one of: histology, morphology, morphometry, and combinations thereof.

* * * * *